United States Patent
Krishnamurthy et al.

(10) Patent No.: US 10,413,891 B1
(45) Date of Patent: Sep. 17, 2019

(54) PROCESS AND APPARATUS FOR REDUCING PRESSURE IN A FLUE GAS STREAM

(71) Applicant: UOP LLC, Des Plaines, IL (US)

(72) Inventors: Sujay R. Krishnamurthy, Hoffman Estates, IL (US); Paolo Palmas, Des Plaines, IL (US); Thomas W. Lorsbach, Austin, TX (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/044,238

(22) Filed: Jul. 24, 2018

(51) Int. Cl.
*B01J 29/90* (2006.01)
*B01J 38/30* (2006.01)
*B01D 53/86* (2006.01)
*C07C 4/06* (2006.01)
*C07C 2/08* (2006.01)

(52) U.S. Cl.
CPC .......... *B01J 29/90* (2013.01); *B01D 53/8696* (2013.01); *B01J 38/30* (2013.01); *C07C 2/08* (2013.01); *C07C 4/06* (2013.01)

(58) Field of Classification Search
CPC . B01J 8/025; B01J 8/0055; B01J 29/90; B01J 38/30; B01J 2208/00539; B01J 2219/00963; B01D 45/12
See application file for complete search history.

(56) References Cited

U.S. PATENT DOCUMENTS

| | | | | |
|---|---|---|---|---|
| 2,545,682 | A * | 3/1951 | Bergman | F01N 1/081 181/254 |
| 2,670,278 | A * | 2/1954 | King | B01J 8/1809 414/294 |
| 2006/0266048 | A1* | 11/2006 | Bell | F01K 23/067 60/783 |

* cited by examiner

*Primary Examiner* — Lessanework Seifu
(74) *Attorney, Agent, or Firm* — Paschall and Maas Law Office; James C. Paschall

(57) ABSTRACT

A process and apparatus for reducing pressure of a flue gas stream comprising passing a pressurized flue gas stream to a vessel and through a bed of particulates in the vessel to reduce the pressure of the flue gas stream. The flue gas passes from the vessel at a lower pressure than at which it entered. The bed of particulates is disposed in the vessel between the outlet end of the inlet conduit and the inlet end of the outlet conduit. If deposits develop in the bed of particulates, the particulates can be replaced with fresh particulates to avoid excessive pressure drop.

16 Claims, 2 Drawing Sheets

PROCESS AND APPARATUS FOR REDUCING PRESSURE IN A FLUE GAS STREAM

FIELD

The field is management of a flue gas stream from a catalyst regenerator and particularly from a catalytic regenerator such as in a fluid catalytic cracking (FCC) unit or a methanol to olefins (MTO) unit.

BACKGROUND

FCC technology has undergone continuous improvement and remains the predominant source of gasoline production in many refineries. This gasoline, as well as lighter products, is formed as the result of cracking heavier, higher molecular weight, less valuable hydrocarbon feed stocks such as gas oil.

In its most general form, the FCC process comprises a reactor that is closely coupled with a regenerator, followed by downstream hydrocarbon product separation. Hydrocarbon feed contacts catalyst in the reactor to crack the hydrocarbons down to smaller molecular weight products. During this process, coke tends to accumulate on the catalyst. Coke must be burned off of the catalyst in a regenerator.

When a catalyst is exposed to oxygenates, such as methanol, to promote a reaction to olefins in a MTO process, carbonaceous material is generated and deposited on the catalyst. Accumulation of coke deposits interferes with the catalyst's ability to promote the MTO reaction. As the amount of coke deposit increases, the catalyst loses activity and less of the feedstock is converted to the desired olefin product. The step of regeneration removes the coke from the catalyst by combustion with oxygen, restoring the catalytic activity of the catalyst. The regenerated catalyst may then be exposed again to oxygenates to promote the conversion to olefins.

Conventional catalyst regenerators typically include a vessel having a spent catalyst inlet, a regenerated catalyst outlet and a combustion gas distributor for supplying air or other oxygen containing gas to the bed of catalyst that resides in the vessel. Cyclone separators remove catalyst entrained in the flue gas before the flue gas exits the regenerator vessel. Downstream vessels which also may utilize cyclonic separation may also be employed to remove catalyst fines from flue gas streams.

The heat of combustion in the regenerator typically produces flue gas at temperatures of 677° to 788° C. (1250° to 1450° F.) and at a pressure range of 138 to 276 kPa (20 to 40 psig). Although the pressure is relatively low, the extremely high temperature, high volume of flue gas from the regenerator contains sufficient kinetic energy to warrant recovery of energy. Flue gas may be fed to a power recovery unit, which may include an expander turbine. The kinetic energy of the flue gas is transferred through blades of the expander to a rotor coupled either to a main air blower, to produce combustion air for the FCC regenerator, and/or to a generator to produce electrical power. The flue gas may also be run to a steam generator for further energy recovery.

Flue gas streams that may have passed through a third stage separator, a flue gas cooler and/or power recovery equipment must still be reduced in pressure before it is exhausted from a stack. Orifice chambers use grids with holes to impose a pressure drop on the flue gas prior to venting through the stack.

More improved pressure reduction vessels can streamline catalyst regenerator flue gas processing.

SUMMARY

A process and apparatus for reducing pressure of a flue gas stream comprises passing a pressurized flue gas stream from a catalyst regenerator to a pressure reduction vessel and through a bed of particulates in the pressure reduction vessel to reduce the pressure of the flue gas stream. The flue gas passes from the vessel at a lower pressure. The bed of particulates is disposed in the vessel between the outlet end of the inlet conduit and the inlet end of the outlet conduit. If deposits develop in the bed of particulates, the particulates can be replaced with fresh particulates to avoid excessive pressure drop. Moreover, the process and apparatus afford the ability to balance pressure drop between the slide valve and the packed bed vessel by changing the packed vessel inventory as the flue gas rate changes.

Additional features and advantages of the invention will be apparent from the description of the invention, figures and claims provided herein.

DEFINITIONS

Figure 1:
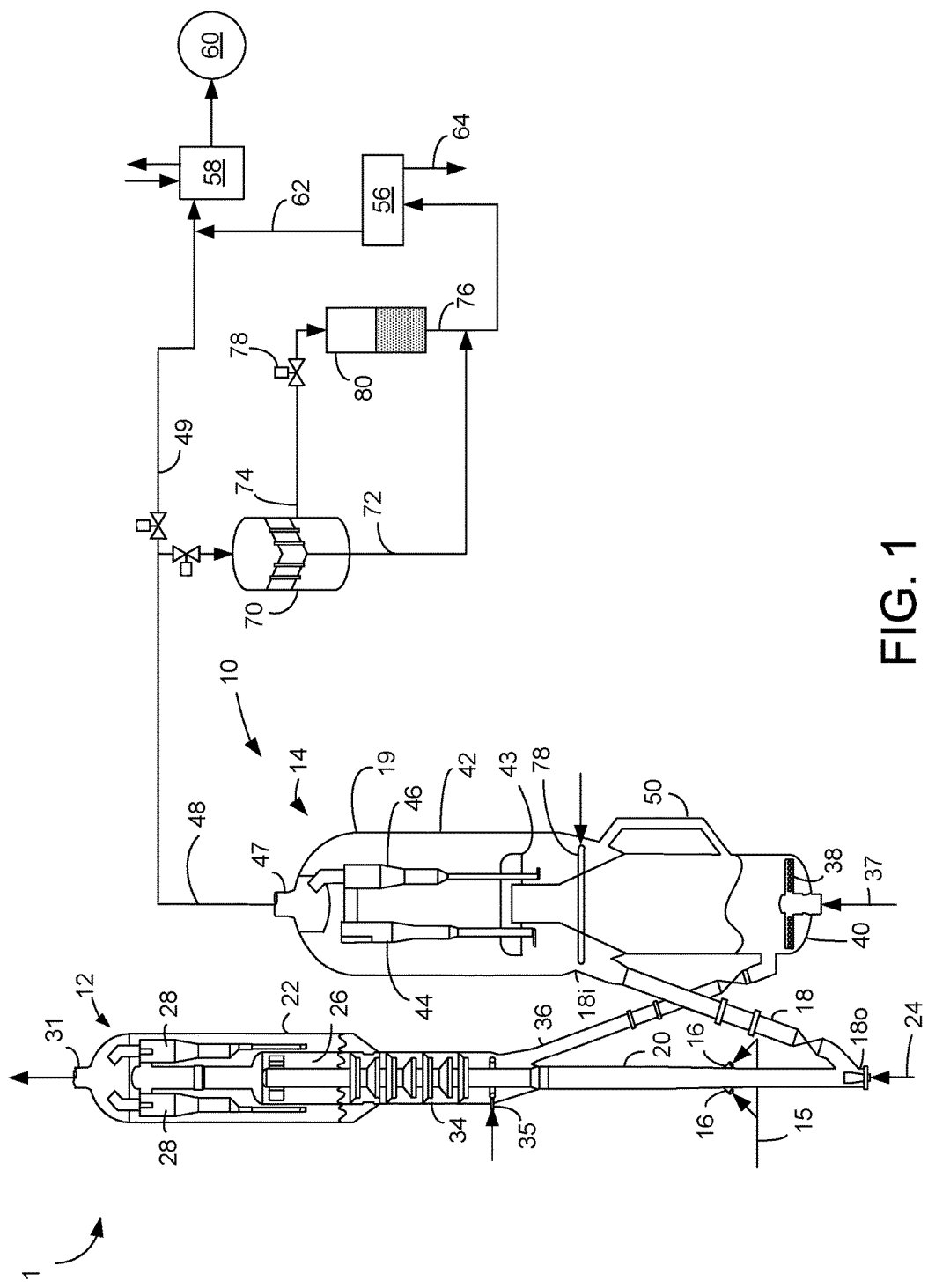
FIG. 1 is a schematic drawing of an FCC unit of the present invention.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without passing through any other intervening vessel.

The term "indirect communication" means that flow from the upstream component enters the downstream component after passing through an intervening vessel.

The term "bypass" means that the object is out of downstream communication with a bypassing subject at least to the extent of bypassing.

As used herein, the term "separator" means a vessel which has an inlet and at least two outlets.

As used herein, the term "predominant" or "predominate" means greater than 50 wt %, suitably greater than 75 wt % and preferably greater than 90 wt %.

As used herein, the term "a component-rich stream" means that the rich stream coming out of a vessel has a greater concentration of the component than the feed to the vessel.

DETAILED DESCRIPTION

We have found that grid holes in conventional orifice chambers are prone to erosion due to the particulate content in the flue gas stream eroding the holes and reducing the degree of pressure drop imposed on the flue gas stream over time. This pressure drop degradation forces the operator to move the upstream slide valve to a more closed position to shift the pressure drop to the upstream slide valve, which could potentially expose the flue gas line to high noise and vibration problems. Further, the higher velocity across the slide valve increases erosion in the valve with corresponding reductions in the useful life of the expensive valves. Pressure drop imbalance can also occur as a result of flue gas rate changes. Moreover, the grid spacing requirements result in tall orifice chambers, especially for larger units. Lastly, in resid FCC units, the formation of eutectic deposits on the holes in the grids result in significant plugging of the holes in the orifice chamber. The refiner often resorts taking the orifice chamber off-line and injecting walnut shells into it to unplug the holes.

The embodiments herein are applicable to replacing perforated plates in an orifice chamber with particulate material which can impose a pressure drop on the passing flue gas stream. If deposits on the particulates become excessive, the depositified particulates can be replenished with clean particulates. The particulate material will not be subjected to erosion since they are not rigidly packed together. Moreover, the particulate material may be constructed from erosion resistant ceramic materials such as alumina and/or silica.

Now turning to the FIG. 1, wherein like numerals designate like components, the FIG. 1 illustrates a process and apparatus 1 for fluid catalytic cracking (FCC). An FCC unit 10 includes a reactor 12 and a regenerator 14. Process variables typically include a cracking reaction temperature of 400 to 600° C. and a catalyst regeneration temperature of 500 to 900° C. Both the cracking and regeneration occur at an absolute positive pressure below about 5 atmospheres.

The FIG. 1 shows a typical FCC process unit, in which a heavy hydrocarbon feed or raw oil stream in a line 15 is distributed by distributors 16 into a riser 20 to be contacted with a newly regenerated cracking catalyst entering from a regenerator conduit 18. This contacting may occur in the narrow riser 20, extending upwardly to the bottom of a reactor vessel 22. The contacting of feed and catalyst is fluidized by gas from a fluidizing line 24. Heat from the catalyst vaporizes the hydrocarbon feed, and the hydrocarbon feed is thereafter cracked to lighter molecular weight hydrocarbons in the presence of the catalyst as both are transferred up the riser 20 into the reactor vessel 22. The cracked light hydrocarbon products are thereafter separated from the cracking catalyst using cyclonic separators which may include a rough cut separator 26 and one or two stages of cyclones 28 in the reactor vessel 22. Product gases exit the reactor vessel 22 through a product outlet 31 for transport to a product recovery section which is not shown. Inevitable side reactions occur in the riser 20 leaving coke deposits on the catalyst that lower catalyst activity. The spent catalyst requires regeneration for further use. Coked catalyst, after separation from the gaseous product hydrocarbon, falls into a stripping section 34 where steam is injected through a nozzle 35 to a distributor to purge any residual hydrocarbon vapor. After the stripping operation, the coked catalyst is fed to the catalyst regenerator 14 through a spent catalyst conduit 36.

The FIG. 1 depicts a regenerator 14 comprising a regenerator vessel 19 known as a combustor. However, other types of regenerators are suitable. In the catalyst regenerator 14, a stream of oxygen-containing gas, such as air, is introduced from a line 37 through an air distributor 38 to contact the spent catalyst in a first, lower chamber 40, combust coke deposited thereon, and provide regenerated catalyst and flue gas. The catalyst regeneration process adds a substantial amount of heat to the catalyst, providing energy to offset the endothermic cracking reactions occurring in the riser 20. Catalyst and air flow upwardly together along a combustor riser located within the catalyst regenerator 14 and, after regeneration, are initially disengaged by discharge into an upper chamber 42 through a disengager 43. Finer separation of the regenerated catalyst and flue gas exiting the disengager 43 is achieved using first and second stage separator cyclones 44, 46, respectively within the upper chamber 42 of the catalyst regenerator 14. Catalyst separated from flue gas dispenses through dip legs from the cyclones 44, 46 while flue gas relatively lighter in catalyst sequentially exits cyclones 44, 46 and is discharged from the regenerator vessel 14 through a flue gas outlet 47 in a flue gas line 48.

Regenerated catalyst may be recycled back to the reactor 12 through the regenerator conduit 18. The riser 20 of the reactor 12 may be in downstream communication with the regenerator vessel 19 of the regenerator 14. The regenerator conduit has an inlet end 18$i$ connecting to the regenerator vessel 19, in an aspect the upper chamber 42 of the regenerator vessel 19, for receiving regenerated catalyst therefrom and an outlet end 18$o$ connecting to the riser 20 of the reactor 12 for transporting regenerated catalyst to the riser 20 of the reactor 12. As a result of the coke burning, the flue gas vapors exiting at the top of the catalyst regenerator 14 in the flue gas line 48 contain $SO_x$, $NO_x$, $CO$, $CO_2$, $N_2$, $O_2$ and $H_2O$, along with smaller amounts of other species. Additionally, some of these species may exit with regenerated catalyst exiting in a regenerator conduit 18 and enter the riser 20 of the reactor 12. In a combustor regenerator shown in the FIG. 1, regenerated catalyst may be transported from the upper chamber 42 into the lower chamber 40 of the regenerator vessel 19 through the catalyst cooler that is not shown and/or through a recycle conduit 50.

Hot flue gas is discharged from the regenerator 14 through the flue gas outlet 47 into a flue gas line 48 in downstream communication with the regenerator 14. A separator may be in downstream communication with the flue gas line 48 for separating regenerated catalyst from the flue gas. Catalyst particles may be separated from discharged flue gas in line 48 by any suitable separator. A suitable separator includes a third stage separator (TSS) 70 which comprises a vessel containing multiple cyclone separators. A TSS 70 may be the separator that is in downstream communication with the regenerator 14. Flue gas discharged in flue gas line 48 may be delivered to the TSS 70 which removes catalyst from flue gas discharged from the regenerator by cyclonic separation. The flue gas line 48 may feed flue gas through an isolation valve to the TSS 70. In the event of upset or other abnormality, flue gas may also bypass the TSS 70 in bypass line 49 through a control valve thereon. The TSS 70 is a vessel that contains a plurality of cyclone separators, which remove a predominance of remaining catalyst particles by centripetal acceleration from the flue gas into an underflow gas line 72. The TSS 70 comprises two tube sheets with a plurality of cyclones extending through the tube sheets. In an aspect, inlets to the cyclones are above both tube sheets, dirty gas outlets of the cyclones are provided between the tube sheets and clean gas outlets are provided below the tube sheets. Clean flue gas exits the TSS 70 in an inlet gas conduit 74. Reference may be had to U.S. Pat. No. 7,316,733 for an example of a TSS vessel. Typically, at least 1 wt % but no more than 10 wt % and preferably no more than 5 wt % of the flue gas that enters the TSS 70 will exit the TSS as dirty gas in the underflow gas line 72 laden with separated regenerated catalyst.

Clean flue gas in the inlet gas conduit 74 exiting the TSS 70 may enter a pressure reduction vessel 80 to reduce its kinetic energy. To control the flow of flue gas between the TSS 70 and the pressure reduction vessel 80, an inlet valve 78 may be provided upstream of the pressure reduction vessel 80 to further control the gas flow entering the pressure reduction vessel 80. The valve 78 may be a control valve and specifically a slide valve that is in communication with the inlet gas conduit 74 for regulating the flow therethrough. The flue gas stream passes through the inlet valve 78 to enter the pressure reduction vessel 80.

The pressure reduction vessel 80 reduces the pressure of the flue gas stream in the inlet gas conduit 74. The clean flue gas stream reduced in pressure in an outlet gas conduit 76 may or may not be joined by underflow gas in underflow gas line 72 through a critical flow nozzle and flow to a steam generator 58 and to an outlet stack 60. The clean flue gas stream reduced in pressure in an outlet gas conduit 76 may also be joined by a bypass flue gas stream in the bypass line 49 before flowing to the steam generator 58 and to the outlet stack 60. Optionally, the combined stream of exhausted clean flue gas and waste gas may be scrubbed in a scrubber and/or have catalyst particulates further removed in an electrostatic precipitator before it is exhausted to the atmosphere in the outlet stack 60. As such, the clean flue gas stream reduced in pressure and perhaps joined by the underflow gas stream in the underflow gas line 72 may be processed in a catalyst fines removal device 56 comprising an electrostatic precipitator or a wet gas scrubber before flowing to the steam generator 58 or the outlet stack 60 in low fines line 62. Fines can be removed from the catalyst fines removal device 56 in fines line 64. The steam generator 58 may also be known as a flue gas cooler which generates steam by cooling the flue gas in line 49 and/or in gas outlet line 76.

The dirty gas stream in underflow line 72 may comprise at least 1 wt % but no more than about 10 wt %, typically no more than about 5 wt %, suitably no more than about 4 wt % of the flue gas fed to the TSS 70 in line 48. The underflow gas in line 72 may have catalyst removed from it in an optional fourth stage separator (not shown) which comprises an additional cyclone separator before combining with the clean flue gas stream reduced in pressure. In an embodiment, a filter (not shown) can be provided as a separator to further remove catalyst that exits the TSS 70 in the dirty gas stream in underflow line 72 by filtration. The underflow gas in line 72 may join the clean flue gas stream in gas outlet line 76 after it is reduced in pressure.

The pressure reduction vessel 80 may be in downstream communication with the inlet gas conduit 74 which is in downstream communication with the catalyst regenerator 14. The pressurized flue gas may be passed from the catalyst regenerator 14 to the pressure reduction vessel 80 via the inlet gas conduit 74.

Figure 2:
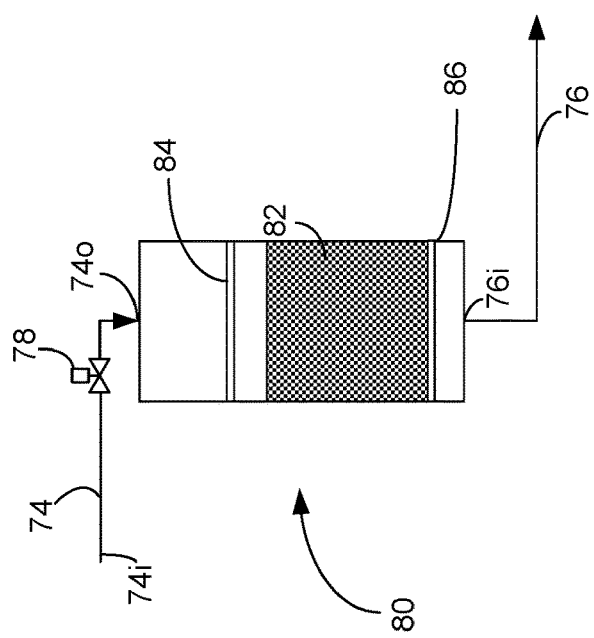
FIG. 2 is an enlarged partial view of FIG. 1.

More detail is given in FIG. 2 for the pressure reduction vessel 80. The pressure reduction vessel 80 may comprise a bed 82 of particulates. The inlet gas conduit 74 has an inlet end 74i in downstream communication with the catalyst regenerator 14 and perhaps the TSS 70 and an outlet end 74o in upstream communication with the bed 82 of particulates. The inlet gas conduit 74 passes the pressurized flue gas stream to the pressure reduction vessel 80. The bed 82 of particulates may be located in the vessel 80 between the outlet 74o of the inlet gas conduit 74 and an inlet 76i of an outlet gas conduit 76, so to pass the pressurized flue gas stream through the bed 82 of particulates in the vessel 80 to reduce the pressure of the flue gas stream.

A flow diffuser 84 upstream of the bed 82 of particulates comprising a perforated plate may spread gas flow across the cross section of the pressure reduction vessel 80 and the bed 82 of particulates. The perforations in the flow diffuser 84 should be at least 25% of the area of the plate so as to not impose the pressure drop on the flue gas stream. The flow diffuser 84 may instead of being flat may be conical, hemispherical or elliptical, such as with a 2:1 ratio of large and small axes.

The particulates in the bed 82 of particulates may comprise inert ceramic balls such as made from alumina and/or silica. For example, each inert ceramic ball may be 2.5, 5 or 7.5 cm (1, 2 or 3 inches) in diameter. Suitable ceramic balls may be commercially available from Saint-Gobain Norpro. Other sizes and types of particulates are contemplated.

A particulate support 86 downstream of the bed 82 of particulates comprising a perforated plate supports the bed 82 of particulates and allows the flue gas stream to pass through the bed 82 of particulates to exit the pressure reduction vessel 80 to the outlet gas conduit 76.

The perforations in the particulate support 86 should be at least 25% of the area of the plate so as to not impose a pressure drop on the flue gas stream. However, the openings must be small enough so as not to allow the particulates to pass through the particulate support 86. The particulate support 86 may instead of being flat may be conical, hemispherical or elliptical, such as with a 2:1 ratio of large and small axes. If conical, the particulate support should be steeper than the angle of repose of the particulates. If the particulates are ceramic balls, the angle of the cone relative to horizontal should be at least 45 degrees.

The pressurized flue gas stream passes through the valve 78, from the outlet 74o of the inlet gas conduit 74, through perforations in the flow diffuser 84 while spreading out across the cross section of the bed 82, travels through the bed of particulates in the vessel 80 to reduce the pressure of the flue gas stream, through the particulate support 86 and exits the vessel 80 through the inlet 76i of the outlet gas conduit 76. The flue gas stream exits from the vessel 80 at a lower pressure than at which it entered. Pressure reduction across the bed 82 can be about 100 kPa (14.5 psi) to about 300 kPa (44 psi) and preferably 138 kPa (20 psi) to about 241 kPa (35 psi).

The outlet gas conduit 76 is in downstream communication with the bed 82 of particulates at an outlet end 76i. The bed 82 of particulates is disposed between the outlet end 74o of the inlet conduit 74 and the inlet end 76i of the outlet conduit 76.

Figure 3:
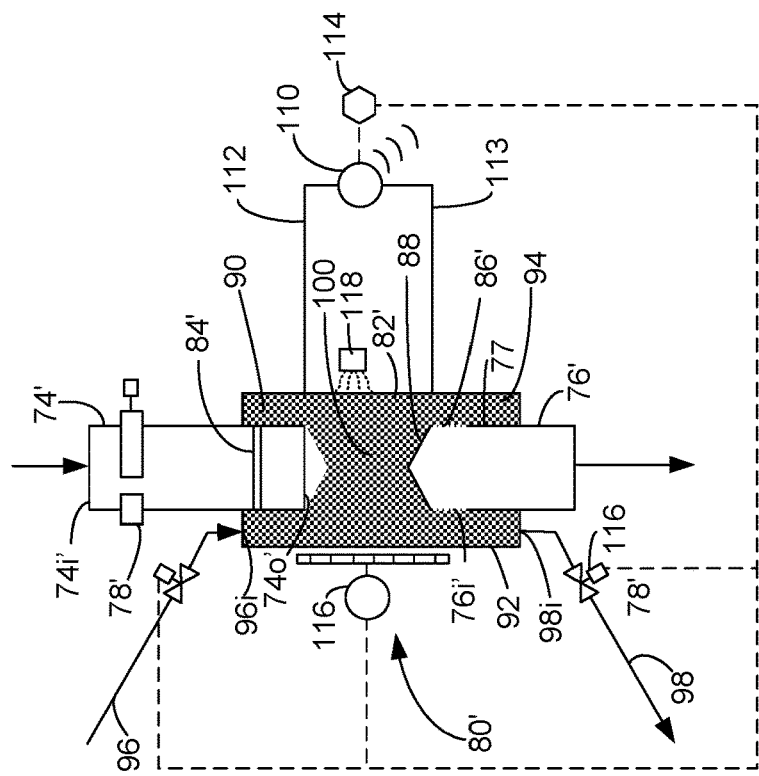
FIG. 3 is an alternative embodiment of FIG. 2.

FIG. 3 is an alternative embodiment of FIG. 2 which dynamically adds and withdraws particulates from the pressure reduction vessel. Many of the elements in FIG. 3 have the same configuration as in FIG. 2 and bear the same reference number. Elements in FIG. 3 that correspond to elements in FIG. 2 but have a different configuration bear the same reference numeral as in FIG. 1 but are marked with a prime symbol (').

In FIG. 3, the pressurized flue gas stream passes through the inlet 74i' of the inlet gas conduit 74', through a valve 78' and through a diffuser 84' which may be contained in the inlet gas conduit to spread the gas flow across the entire cross section of the inlet gas conduit. The pressurized flue gas exits an outlet 74o' of the inlet gas conduit 74' and enters into the bed 82' of particulates. The particulates may leave a conical gap between its upper surface and the outlet 74o' having an angle equivalent to the angle of repose of the particulates. The flue gas travels across the bed 80' of particulates and exits through an inlet 76i' to the outlet gas conduit 76'. The outlet gas conduit 76' may have a closed inlet end 88 and the inlet 76i' may be disposed in the side 77 of the outlet gas conduit 76'. The closed inlet end 88 may comprise a conical top that has an angle relative to horizontal equivalent to the angle of repose of the particulates in the bed 82'. The inlet 76i' may comprise perforations in a side 77 of the outlet gas conduit 76 that comprise at least 25% open area in the vicinity of the inlet 76i' but small enough, so that the particulates may not pass through, so as to provide a particulate support 86'. The flue gas reduced in pressure passes into the outlet conduit 76 through a side 77 of said outlet conduit where the inlet 76i' is located. The pressure drop across the bed of particulates between the outlet 74o' of the inlet gas conduit 74' and an inlet 76i' of the outlet gas conduit 76' reduces the pressure of the flue gas stream.

The inlet gas conduit 74' may have its outlet end extend into the pressure reduction vessel 80' so as to define an inlet annulus 90 between the wall 94 of the vessel 80 and the inlet gas conduit 74', and the outlet gas conduit 76' may have its inlet end extend into the pressure reduction vessel, so as to define an outlet annulus 92 between the wall 94 of the vessel 80 and the outlet conduit 76'.

Particulates may be added to the vessel 80' and removed from the vessel as they accumulate deposits from the flue gas flow or as desired to shift the pressure drop balance due to changes in throughput. A particulate inlet 96i in the vessel 80' on the end of a particulate addition line 96 may add particulates to the bed 82' of particulates. The particulate inlet 96i may be located at a location that does not receive gas flow, such as in the inlet annulus 90. As particulates are added to the inlet annulus 90, they make their way to an active area 100 of the bed 82' between the outlet 74o' of the gas inlet conduit 74' and the inlet 76i' of the gas outlet conduit 76' that receives gas flow. A particulate outlet 98i in the vessel 80' on the end of a particulate removal line 98 may withdraw particulates from the bed 82' of particulates. The particulate outlet 98i may be located at a location that does not receive gas flow, such as in the outlet annulus 94. As particulates are withdrawn from the outlet annulus 94, they make room for other added particulates to make their way into the active area 100 of the bed 82' between the inlet 74o' and the outlet 76i'. Because the inlet annulus 90 and the outlet annulus are remote from the active area 100, they do not receive gas flow.

The apparatus of FIG. 3 may also include a pressure drop indicator 110 that measures pressure in the pressure reduction vessel 80' between two taps 112, 113 located in the bed 82' of particulates. The pressure drop indicator 110 transmits a signal of the measured pressure drop to a computer 114. The pressure drop indicator 110 may transmit a signal wirelessly. When deposits accumulate on the particulates, pressure drop across the bed increases. If the measured pressure drop exceeds a predetermined value of pressure drop, the computer 114 signals a control valve 116 which may be on the particulate removal line 98 to open or open more to allow particulates or to allow more particulates to exit the particulate outlet 98i from the vessel 80 and the bed 82' of particulates. When an inlet valve on the particulate addition line 96 is open, discharge of particles through the particle outlet 98i into the particulate removal line 98 will allow particulates to enter the vessel 80 via the particle inlet 96i to the inlet annulus 90. Addition of fresh particulates will reduce pressure drop due to their absence of deposits.

When the measured pressure drop no longer exceeds the predetermined pressure drop, the computer 114 signals the control valve 116 on the particulate removal line 98 to close or to close more than it was thus disallowing or restricting particulates to exit the particulate outlet 98i. The computer 114 may also send a signal to a control valve on the particulate addition line 96 to cooperate with the control process. The vessel 80' may also be equipped with a level indicator 116 which may operate by registering the transmittance of gamma rays at different levels emitted from a gamma ray source 118.

Any of the above lines, units, separators, columns, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring components, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

SPECIFIC EMBODIMENTS

While the following is described in conjunction with specific embodiments, it will be understood that this description is intended to illustrate and not limit the scope of the preceding description and the appended claims.

A first embodiment of the invention is a process for reducing pressure of a flue gas stream comprising passing a pressurized flue gas stream to a vessel; passing the pressurized flue gas stream through a bed of particulates in the vessel to reduce the pressure of the flue gas stream; and passing the flue gas stream from the vessel at a lower pressure. An embodiment of the invention is one, any or all of prior embodiments in this paragraph up through the first embodiment in this paragraph further comprising passing the pressurized flue gas through a diffuser to spread the flow of flue gas over a cross section. An embodiment of the invention is one, any or all of prior embodiments in this paragraph up through the first embodiment in this paragraph further comprising passing the flue gas from a catalyst regenerator to the vessel. An embodiment of the invention is one, any or all of prior embodiments in this paragraph up through the first embodiment in this paragraph further comprising passing the flue gas stream through a valve to enter the vessel. An embodiment of the invention is one, any or all of prior embodiments in this paragraph up through the first embodiment in this paragraph further comprising removing particulates from the vessel and adding particulates to the vessel. An embodiment of the invention is one, any or all of prior embodiments in this paragraph up through the first embodiment in this paragraph further comprising measuring a pressure drop between two taps in the vessel, comparing the pressure drop to a predetermined value and adding fresh particulates to the vessel. An embodiment of the invention is one, any or all of prior embodiments in this paragraph up through the first embodiment in this paragraph further comprising passing the flue gas stream from an inlet conduit into the vessel and withdrawing the flue gas from the vessel in an outlet conduit, the flue gas passing into the outlet conduit through a side of the outlet conduit.

A second embodiment of the invention is a vessel for reducing pressure of a flue gas stream comprising a vessel comprising a bed of particulates; an inlet gas conduit in communication with a catalyst regenerator at an inlet end and an outlet end of the inlet conduit in communication with the bed of particulates; an outlet gas conduit in communication with the bed of particulates at an inlet end; the bed of particulates between the outlet end of the inlet conduit and the inlet end of the outlet conduit. An embodiment of the invention is one, any or all of prior embodiments in this paragraph up through the second embodiment in this paragraph further comprising a particulate inlet in the vessel for adding particulates to the bed of particulates. An embodiment of the invention is one, any or all of prior embodiments in this paragraph up through the second embodiment in this paragraph wherein the particulate inlet is in a portion of the vessel that does not receive gas flow. An embodiment of the invention is one, any or all of prior embodiments in this paragraph up through the second embodiment in this paragraph wherein the particulate inlet is in an annulus defined between the inlet gas conduit extending into the vessel and a wall of the vessel. An embodiment of the invention is one, any or all of prior embodiments in this paragraph up through the second embodiment in this paragraph further comprising a particulate outlet in the vessel for withdrawing particulates from the bed of particulates. An embodiment of the invention is one, any or all of prior embodiments in this paragraph up through the second embodiment in this paragraph wherein the particulate outlet is in an annulus defined between the outlet gas conduit extending into the vessel and a wall of the vessel. An embodiment of the invention is one, any or all of prior embodiments in this paragraph up through the second embodiment in this paragraph wherein the outlet gas conduit has a closed end and an inlet disposed in the side of the conduit. An embodiment of the invention is one, any or all of prior embodiments in this paragraph up through the second embodiment in this paragraph further comprising a valve in communication with the inlet gas conduit. An embodiment of the invention is one, any or all of prior embodiments in this paragraph up through the second embodiment in this paragraph further comprising a flow diffuser upstream of the bed of particulates to spread gas flow across the cross section of the bed of particulates. An embodiment of the invention is one, any or all of prior embodiments in this paragraph up through the second embodiment in this paragraph, further comprising at least one of a sensor in fluid communication with the vessel for sensing at least one parameter; and a transmitter in communication with the device for transmitting a signal or data from the sensor.

A third embodiment of the invention is a vessel for reducing pressure of a flue gas stream comprising a vessel comprising a bed of particulates; an inlet gas conduit in communication with a catalyst regenerator at an inlet end and an outlet end of the inlet conduit in communication with the bed of particulates; a particulate inlet in the vessel for adding particulates to the bed of particulates, the particulate inlet located in a portion of the vessel that does not receive gas flow; an outlet gas conduit in communication with the bed of particulates at an inlet end; a particulate outlet in the vessel for withdrawing particulates from the bed of particulates, the particulate outlet located in a portion of the vessel that does not receive gas flow; and the bed of particulates between the outlet end of the inlet conduit and the inlet end of the outlet conduit. An embodiment of the invention is one, any or all of prior embodiments in this paragraph up through the third embodiment in this paragraph wherein the particulate inlet is in an annulus defined between the inlet gas conduit extending into the vessel and a wall of the vessel and the particulate outlet is in an annulus defined between the outlet gas conduit extending into the vessel and the wall of the vessel. An embodiment of the invention is one, any or all of prior embodiments in this paragraph up through the third embodiment in this paragraph wherein the outlet gas conduit has a closed end and an inlet disposed in the side of the conduit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for reducing pressure of a flue gas stream comprising:
   passing a pressurized flue gas stream to a vessel, the vessel comprising a bed of particulates and an inlet gas conduit in communication with a catalyst regenerator at an inlet end and an outlet end of said inlet gas conduit in communication with said bed of particulates;
   adding particulates to said bed of particulates through a particulate inlet in said vessel, said particulate inlet is in a portion of said vessel that does not receive gas flow, said particulate inlet is in an annulus defined between said inlet gas conduit extending into said vessel and a wall of said vessel;
   passing the pressurized flue gas stream through said bed of particulates in the vessel to reduce the pressure of the flue gas stream; and
   passing the flue gas stream from the vessel at a lower pressure.

2. The process of claim 1 further comprising passing the pressurized flue gas through a diffuser to spread the flow of flue gas over a cross section.

3. The process of claim 1 further comprising passing the flue gas from the catalyst regenerator to said vessel.

4. The process of claim 1 further comprising passing the flue gas stream through a valve to enter the vessel.

5. The process of claim 1 further comprising removing particulates from the vessel and adding particulates to the vessel.

6. The process of claim 1 further comprising measuring a pressure drop between two taps in the vessel, comparing the pressure drop to a predetermined value and adding fresh particulates to the vessel.

7. The process of claim 1 further comprising passing the flue gas stream from an inlet conduit into said vessel and withdrawing the flue gas from the vessel in an outlet conduit, the flue gas passing into the outlet conduit through a side of said outlet conduit.

8. A vessel for reducing pressure of a flue gas stream comprising:
   a vessel comprising a bed of particulates;
   an inlet gas conduit in communication with a catalyst regenerator at an inlet end and an outlet end of said inlet conduit in communication with said bed of particulates;
   an outlet gas conduit in communication with said bed of particulates at an inlet end;
   a particulate inlet in said vessel for adding particulates to said bed of particulates;
   a particulate outlet in said vessel for withdrawing particulates from said bed of particulates;
   said particulate outlet is in an annulus defined between said outlet gas conduit extending into said vessel and a wall of said vessel; and
   said bed of particulates between the outlet end of the inlet conduit and the inlet end of the outlet conduit.

9. The vessel of claim 8 wherein said particulate inlet is in a portion of said vessel that does not receive gas flow.

10. The vessel of claim 9 wherein said particulate inlet is in an annulus defined between said inlet gas conduit extending into said vessel and a wall of said vessel.

11. The vessel of claim 8 wherein said outlet gas conduit has a closed end and an inlet disposed in the side of the conduit.

12. The vessel of claim 8 further comprising a valve in communication with said inlet gas conduit.

13. The vessel of claim 8 further comprising a flow diffuser upstream of said bed of particulates to spread gas flow across the cross section of the bed of particulates.

14. The vessel of claim 8, further comprising at least one of:
   a sensor in fluid communication with the vessel for sensing at least one parameter; and
   a transmitter in communication with said vessel for transmitting a signal or data from the sensor.

15. A vessel for reducing pressure of a flue gas stream comprising:
   a vessel comprising a bed of particulates;
   an inlet gas conduit in communication with a catalyst regenerator at an inlet end and an outlet end of said inlet conduit in communication with said bed of particulates;
   a particulate inlet in said vessel for adding particulates to said bed of particulates, said particulate inlet located in a portion of said vessel that does not receive gas flow;
   an outlet gas conduit in communication with said bed of particulates at an inlet end, said outlet gas conduit has a closed end and an inlet disposed in the side of the conduit;
   a particulate outlet in said vessel for withdrawing particulates from said bed of particulates, said particulate outlet located in a portion of said vessel that does not receive gas flow; and
   said bed of particulates between the outlet end of the inlet conduit and the inlet end of the outlet conduit.

16. The vessel of claim 15 wherein said particulate inlet is in an annulus defined between said inlet gas conduit extending into said vessel and a wall of said vessel and said particulate outlet is in an annulus defined between said outlet gas conduit extending into said vessel and said wall of said vessel.

* * * * *